| United States Patent [19] | [11] Patent Number: 5,021,178 |
|---|---|
| Chen et al. | [45] Date of Patent: Jun. 4, 1991 |

[54] ACYLATION OF LOWER OLEFIN OLIGOMERS

[75] Inventors: Catherine S. H. Chen, Berkley Heights; Paul G. Rodewald, Rocky Hill, both of N.J.

[73] Assignee: Mobil Oil Corporation, Fairfax, Va.

[21] Appl. No.: 476,080

[22] Filed: Feb. 7, 1990

[51] Int. Cl.$^5$ ................. C10M 105/20; C10M 129/24
[52] U.S. Cl. .................................. 252/52 R; 568/397; 568/398
[58] Field of Search ............... 568/394, 395, 397, 398; 252/52 R

[56] References Cited

U.S. PATENT DOCUMENTS

| 2,297,039 | 9/1942 | van Melson | 568/395 |
|---|---|---|---|
| 2,315,046 | 3/1943 | Byrns | 568/397 |
| 2,355,703 | 8/1944 | Byrns | 568/397 |
| 2,411,823 | 11/1946 | Doumani et al. | 568/397 |
| 2,457,696 | 12/1948 | Lukes et al. | 568/397 |
| 3,030,359 | 4/1962 | Arens | 568/395 |
| 4,520,221 | 5/1985 | Chen | 585/517 |
| 4,568,786 | 2/1986 | Chen et al. | 585/517 |
| 4,658,079 | 4/1987 | Chen | 585/517 |

*Primary Examiner*—Prince E. Willis
*Assistant Examiner*—E. M. McAvoy
*Attorney, Agent, or Firm*—Alexander J. McKillop; Charles J. Speciale; Malcolm D. Keen

[57] ABSTRACT

Oligomers produced from lower alkenes by acidic zeolite catalyzed oligomerization can be converted to useful lubricant additives or lubricants by acylation of olefinic bonds in the oligomers, whereby oligomers containing alpha, beta unsaturated ketone structures are produced. The products so produced from $C_{20}+$ olefins exhibit favorable lubricant qualities of viscosity index and low pour points. The discovery is particularly applicable to the acylation of oligomers produced from lower alkenes such as propylene by oligomerization using a ZSM-5 catalyst which has been surface deactivated.

7 Claims, No Drawings

ACYLATION OF LOWER OLEFIN OLIGOMERS

This invention relates to processes for the acylation of oligomers of lower olefins and to the products produced thereby exhibiting lubricant properties and lubricant additive qualities. In particular, the invention relates to the acid catalyzed acylation with carboxylic acid anhydrides of unique olefinic oligomers obtained by oligomerization of lower olefins using zeolite catalysis. The novel acylated products are useful, inter alia, as lubricants having high viscosity index and low pour point. The invention further relates to mixtures of these novel derivitized oligomers with mineral oil and synthetic lubricant systems and their utilization as additives for lubricant compositions.

BACKGROUND OF THE INVENTION

Recent work in the field of olefin upgrading has resulted in a catalytic process for converting lower olefins to heavier hydrocarbons. Heavy distillate and lubricant range hydrocarbons can be synthesized over ZSM-5 type catalysts at elevated temperature and pressure to provide a product having substantially linear molecular conformations due to the ellipsoidal shape selectivity of certain medium pore catalysts.

Conversion of olefins to gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of a ZSM-5 type zeolite. Particular interest is shown in a technique developed by Garwood, et al., as disclosed in European patent application No. 83301391.5, published Sept. 29, 1983. In U.S. Pat. Nos. 4,150,062; 4,211,640 and 4,227,992 Garwood et al disclose the operating conditions for the Mobil Olefin to Gasoline/Distillate (MOGD) process for selective conversion of $C_3+$ olefins to mainly aliphatic hydrocarbons.

In the process for catalytic conversion of olefins to heavier hydrocarbons by catalytic oligomerization using a medium pore shape selective acid crystalline zeolite, such as ZSM-5 type catalyst, process conditions can be varied to favor the formation of hydrocarbons of varying molecular weight. At moderate temperature and relatively high pressure, the conversion conditions favor $C_{10}+$ aliphatic product Lower olefinic feedstocks containing $C_2-C_8$ alkenes may be converted; however, the distillate mode conditions do not convert a major fraction of ethylene. A typical reactive feedstock consists essentially of $C_3-C_6$ mono-olefins, with varying amounts of nonreactive paraffins and the like being acceptable components.

U.S. Pat. Nos. 4,520,221, 4,568,786 and 4,658,079 to C. S. H. Chen et al., incorporated herein by reference in their entirety, disclose further advances in zeolite catalyzed olefin oligomerization. These patents disclose processes for the preparation of high viscosity index lubricant range hydrocarbons by oligomerization of light olefins using zeolite catalyst such as ZSM-5. The oligomers so produced are essentially linear in structure and contain olefin unsaturation. These unique olefinic oligomers are produced by surface deactivation of the ZSM-5 type catalyst by pretreatment with a surface-neutralizing base.

The formulation of lubricants typically includes an additive package incorporating a variety of chemicals to improve or protect lubricant properties in application specific situations, particularly internal combustion engine and machinery applications. The more commonly used additives include oxidation inhibitors, rust inhibitors, antiwear agents, pour point depressants, detergent-dispersants, viscosity index (VI) improvers, foam inhibitors and the like. This aspect of the lubricant arts is specifically described in Kirk-Othmer "Encyclopedia of Chemical Technology", 3rd edition, Vol. 14, pp 477-526, incorporated herein by reference. The inclusion of additives in lubricants provides a continuing challenge to workers in the field to develop improved additives of increased compatibility with the lubricant and other additives or new additives containing a multifunctional capability that can reduce the number of additives required in the formulation.

The olefinic character of the lower olefin oligomers produced by the aforenoted ZSM-5 catalyzed processes of Chen et al. provides a reactive site to modify those unique oligomers to produce derivatives that can exhibit lube additive properties or improvements in lubricant characteristics or improvement in additive solubility in the base stock. Known derivation reactions of conventional alkenes or olefins include acylation with acyl halides or carboxylic acid anhydrides with Friedel-Crafts type catalysts as described in Advanced Organic Chemistry by E. Earl Royals, pp 381-385, Prentice-Hall, Inc. publisher, and incorporated herein by reference. Using acyl halides as acylating agent results in addition of the acyl moiety and chlorine across the olefinic double bond to produce the corresponding chloroketone which can be dehydrohalogenated to produce an alpha, beta unsaturated ketone. However, it is known that acylation of olefins with carboxylic acid anhydrides using stannic chloride as catalyst produces the alpha, beta unsaturated ketone directly. Acylation of oligomeric alkenes or olefins can, therefore, produce acylated products containing ketone and olefinic unsaturation functionalities which can be used to synthesize further additives or which can exhibit lubricant or additive properties in their own right.

Accordingly, it is an object of the present invention to provide a process for the acylation of olefins or alkenes produced by the zeolite catalyzed oligomerization of lower olefins or alkenes.

It is another object of the present invention to provide novel lubricant additives and lubricants by the acylation of olefin oligomers produced from lower olefins by surface deactivated zeolite catalysts.

Yet another object of the instant invention is to provide novel lubricant mixtures from mineral oil and synthetic lubricants derived from polyalphaolefins and containing lower alkene oligomers containing ketone groups.

SUMMARY OF THE INVENTION

It has been discovered that the oligomers produced from lower alkenes or olefins by acidic zeolite catalyzed oligomerization can be converted to useful lubricant additives or lubricants by acylation of olefinic bonds in the oligomers, whereby oligomers containing alpha, beta unsaturated ketone structures are produced. The products so produced from $C_{20}+$ olefins exhibit favorable lubricant qualities of viscosity index and low pour points. The discovery is particularly applicable to the acylation of oligomers produced from lower olefins or alkenes such as propylene by oligomerization using a ZSM-5 catalyst which has been surface deactivated.

More particularly, a reaction product comprising an alpha, beta unsaturated ketone has been discovered wherein the product is made by acylation of an oligomeric olefin with an acylating agent comprising carboxylic acid anhydride in contact with acidic acylation catalyst. The oligomeric olefin comprises the oligomerization product of lower olefin oligomerized in contact with medium pore, shape selective metallosilicate catalyst under oligomerization conditions. The product comprises a liquid lubricant containing $C_{20}+$ carbon atoms and having a viscosity at 100° C. greater than 2 cS and viscosity index measured at 100° C. greater than 70.

The invention further comprises a process for the production of liquid lubricant or lubricant additive comprising contacting a mixture comprising a carboxylic acid anhydride and alkene oligomer containing greater than twenty carbon atoms with acidic catalyst comprising Lewis acid catalyst, including $AlCl_3$, $FeCl_3$, $SnCl_4$, $BF_3$ and $ZnCl_2$ and the like, under acylation reaction conditions wherein the alkene oligomer comprises the oligomerization product of lower alkene oligomerized in contact with medium pore, shape selective metallosilicate catalyst under oligomerization conditions. Separating of the reaction product results in recovery of liquid lubricant or additive containing alpha, beta unsaturated ketone groups.

The invention also pertains to liquid lubricant compositions comprising a mixture of a liquid hydrocarbon lubricant and the lubricant additive made according to the foregoing process. The mixtures may further contain lubricant additives taken from the group consisting of dispersants, detergents, viscosity index improvers, extreme pressure/antiwear additives, antioxidants, pour point depressants, emulsifiers, demulsifiers, corrosion inhibitors, antirust inhibitors, antistaining additives, friction modifiers, and the like.

DETAIL DESCRIPTION OF THE INVENTION

The olefin oligomers used as starting material in the present invention are prepared from $C_2$-$C_{10}$ olefins according to the methods presented by Chen et al. in the aforementioned patents cited and incorporated as references shape-selective oligomerization, as it applies to conversion of $C_2$-$C_{10}$ olefins over ZSM-5, is known to produce higher olefins up to $C_{30}$ and higher. Reaction conditions favoring higher molecular weight products are low temperature (200°-260° C.), elevated pressure (about 2000 kPa or greater) and long contact times (less than 1 WHSV). The reaction under these conditions proceeds through the acid catalyzed steps of oligomerization, isomerization-cracking to a mixture of intermediate carbon number olefins, and interpolymerization to give a continuous boiling product containing all carbon numbers. The channel system of ZSM-5 type catalysts impose shape selective constraints on the configuration of large molecules, accounting for the differences with other catalysts.

The shape-selective oligomerization/polymerization catalysts preferred for use herein to prepare the olefin oligomers used as starting material in the invention include the crystalline aluminosilicate zeolites having a silica to alumina molar ratio of at least 12, a constraint index of about 1 to 12 and acid cracking activity of about 50–300. Representative of the ZSM-5 type zeolites are ZSM-5, ZSM-11, ZSM-12, ZSM-23, ZSM-35 and ZSM-38. ZSM-5 is disclosed and claimed in U.S. Pat No. 3,702,886 and U.S. Pat. Re. No. 29,948; ZSM-11 is disclosed and claimed in U.S. Pat. No. 3,709,979. Also, see U.S. Pat. Nos. 3,832,449 for ZSM-12; 4,076,842 for ZSM-23; 4,016,245 for ZSM-35 and 4,046,839 for ZSM-38. The disclosures of these patents are incorporated herein by reference. A suitable shape selective medium pore catalyst for fixed bed is a small crystal H-ZSM-5 zeolite (silica:alumina ratio=70:1) with alumina binder in the form of cylindrical extrudates of about 1–5mm. Unless otherwise stated in this description, the catalyst shall consist essentially of ZSM-5, which has a crystallite size of about 0.02 to 0.05 micron. Other pentasil catalysts which may be used in one or more reactor stages include a variety of medium pore siliceous material disclosed in U.S. Pat. Nos. 4,414,423 and 4,417,088, incorporated herein by reference.

The acid catalysts are deactivated by pretreatment with a surface-neutralizing base, as disclosed by Chen in the patents incorporated by reference.

Considering propylene oligomerization for purposes of illustration, the olefinic oligomerization-polymerization products include $C_{10}+$ substantially linear aliphatic hydrocarbons. The ZSM-5 catalytic path for propylene feed provides a long chain with approximately one lower alkyl (e.g., methyl) substituent per 8 or more carbon atoms in the straight chain. The lubricant range product can be depicted as a typical linear molecule having a sparingly-substituted long carbon chain with some olefinic unsaturation.

Olefinic oligomer lube range materials can be obtained in a two-stage process or a single stage process. Generally, in a two stage process the first stage involves oligomerization of an inexpensive lower olefin of, e.g., propylene at about 200° C. over a surface poisoned HZSM-5. The second stage involves further oligomerization/interpolymerization of the product (or a fraction of the product) from the first stage over a second and/or different acid catalyst, which may be modified or unmodified as disclosed herein, at about 100°-260° C. The temperature of the second state is about 25°-75° C. lower and preferably the catalyst is an unmodified ZSM-5 type catalyst. Both high yields and high VI are achieved by this two-stage process. In a single stage process only the first stage of the two stage process is employed. Lubes of extremely high VI are achieved, but at a lower yield.

Conventional temperatures, pressures and equipment may be used in the oligomerization process. Preferred temperatures may vary from about 100° C. to about 350° C. , preferably 150° C. to 250° C. pressures from about atmospheric to 20,000 kPa (3000 psi) and WHSV from about 0.01 to about 2.0, preferably 0.2 to 1.0 are employed.

The Friedel-Crafts acylation of the foregoing oligomeric alkenes can be carried out in the present invention using acyl halides or carboxylic acid anhydrides as acylating agent, although acid anhydrides are preferred. The products of the invention are oligomeric alpha, beta unsaturated ketones. In general, the overall reaction is illustrated as follows:

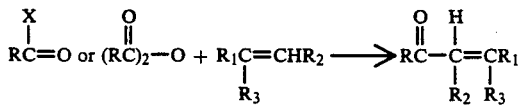

where x is halogen, R is alkyl, aryl or aralkyl and $R_1$, $R_2$ and $R_3$ is alkyl.

When the acylation of the oligomeric alkene is conducted using acyl halide the initial product is the halo alkyl ketone addition product to the olefinic bond. To obtain the desired alpha beta unsaturated ketone the halogen containing product is dehydrohalogenated under mild conditions using substances such as sodium carbonate and procedures well known in the art. In the preferred embodiment of the invention the acylating agent is carboxylic acid anhydride and the process is conducted employing Friedel-Crafts catalysts such as $AlCl_3$, $FeCl_3$, $SnCl_4$, $BF_3$, $ZnCl_2$ or other Lewis acid catalysts. Acidic zeolite may also be used as catalyst for the acylation reaction. The preferred catalyst for acylating the alkene oligomer with acid anhydride is stannic chloride, $SnCl_4$.

Useful carboxylic acid anhydrides in the present invention include both aliphatic and aromatic anhydrides containing four to twenty carbon atoms. Particularly useful anhydrides include acetic, propionic, butyric, valeric, hexanoic, heptanoic, octanoic, benzoic, phenylacetic and naphthoic. The preferred anhydride is acetic anhydride.

The overall reaction temperature for acylation using acid anhydrides can be between $-20°$ C. and $200°$ C. at subatmospheric, atmospheric or supra-atmospheric pressures. Preferably, the reaction is carried out batchwise by the addition of the acid anhydride to a mixture of the olefin oligomer and catalyst. An inert solvent may be used. The product is isolated by conventional means to provide the unsaturated ketone oligomer in high yield. Infrared analysis of the product shows ketone and olefinic unsaturation absorptions typical of alpha, beta unsaturated ketones.

The following Example illustrates the present invention employing acetic anhydride as acylating agent.

EXAMPLE 1

Acylation of olefins having the average composition $C_{25}H_{50}$ is carried out at $33°$ C. To a rapidly stirred mixture of olefin (17.53 g, 0.0500 mole) and stannic chloride (8.868 g, 0.0333 mole) is added dropwise 3.40 g (0.0333 mole) acetic anhydride. The acylated product weighs 18.91 g, shows a ketone carbonyl absorption at 1711 $cm^{-1}$ in its infrared spectrum, and contains 4.54% oxygen by elemental analysis. The following table compares the viscometric properties of the starting olefin with those of the acylated product.

|  | Fresh | Acylated |
| --- | --- | --- |
| Viscosity at 100° C. | 2.8 | 4.0 |
| Viscosity Index (100° C.) | 93 | 72 |

It has been determined that the products of the instant invention produce novel lubricant mixtures when mixed with the hydrocarbon lubricants known in the art, including mineral oil and synthetic lubricants such as those derived from the oligomerization of alphaolefins in contact with cationic and Ziegler catalyst. The sulfonated and/or amidated oligomers can be added to the lubricants in amounts ranging from 0.1% to 99% by mixing. The mixtures may further contain lubricant additives taken from the group consisting of dispersants, detergents, viscosity index improvers, extreme pressure/antiwear additives, antioxidants, pour point depressants, emulsifiers, demulsifiers, corrosion inhibitors, antirust inhibitors, antistaining additives, friction modifiers, and the like.

While the instant invention has been described by specific examples and embodiments, there is no intent to limit the inventive concept except as set forth in the following claims.

What is claimed is:

1. A process for the production of liquid lubricant or lubricant additive comprising;

contacting an oligomeric olefin and a carboxylic acid anhydride under acylating conditions in contact with acidic acylation catalyst, said olefin comprising the oligomerization product of lower olefin oligomerized in contact with medium pore, shape selective metallosilicate catalyst under oligomerization conditions;

separating the acylation reaction product and recovering said liquid lubricant or additive containing alpha, beta unsaturated ketone.

2. The process of claim 1 wherein said acid anhydride includes aliphatic and aromatic mono and dicarboxylic acid anhydride.

3. The process of claim 1 wherein said acid anhydride includes acetic, propionic, butyric, valeric, hexanoic, heptanoic, octanoic, benzoic, phenylacetic and naphthoic.

4. The process according to claim 1 wherein said liquid lubricant contains $C_{20}+$ carbon atoms having a viscosity at 100° C. greater than 2 cS and viscosity index greater than 70.

5. The process according to claim 1 wherein said metallosilicate catalyst comprises ZSM-5 catalyst.

6. The process according to claim 5 wherein the surface of said catalyst is rendered substantially inactive for acid reactions by treatment with a surface deactivating agent.

7. The process according to claim 1 wherein said acylation catalyst includes $AlCl_3$, $FeCl_3$, $SnCl_4$, $BF_3$ and $ZnCl_2$.

* * * * *